United States Patent [19]

Georgiev et al.

[11] 4,179,460
[45] Dec. 18, 1979

[54] DERIVATIVES OF R,S-[X2-(2-HYDROXYETHYLAMINO)-1-PHENYL]-ETHYLAMINE, AND PROCESS

[75] Inventors: Atanas G. Georgiev; Hristo P. Daskalov; Ventzel G. Michaylov; Kina V. Konstantinova, all of Sofia, Bulgaria

[73] Assignee: DSO "Pharmachim", Sofia, Bulgaria

[21] Appl. No.: 921,003

[22] Filed: Jun. 30, 1978

[30] Foreign Application Priority Data

Jul. 6, 1977 [BG] Bulgaria .................................. 37908

[51] Int. Cl.² ........................................... C07C 153/09
[52] U.S. Cl. ............................................. 260/455 R
[58] Field of Search ................................... 260/455 R

[56] References Cited

FOREIGN PATENT DOCUMENTS 2236970  7/1972  Fed. Rep. of Germany ...... 260/455 R

Primary Examiner—John M. Ford
Assistant Examiner—Robert C. Whittenbaugh
Attorney, Agent, or Firm—Karl F. Ross

[57] ABSTRACT

An R,S-[2-(2-hydroxyethylamino)-1-phenyl]-ethylamine of the formula III

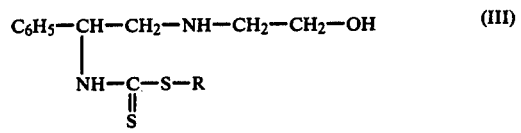

wherein R represents hydrogen, allyl, propargyl or benzyl. These compounds provide valuable intermediates for the synthesis of Tetramisole.

4 Claims, No Drawings

DERIVATIVES OF R,S-[X2-(2-HYDROXYETHYLAMINO)-1-PHENYL]-ETHYLAMINE, AND PROCESS

This invention relates to R,S-[[2-(2-hydroxyethylamino)-1-phenyl]-ethylamine derivatives which are valuable intermediates with production of R,S-2,3,5,6-tetrahydro-6-phenyl-imidazo(2,1-b)-thiazole, of Formula I

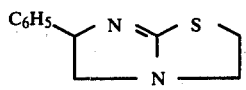

also known as Tetramisole, and its pharmaceutically-acceptable salts with inorganic and organic acids. The invention also relates to a process for producing these compounds.

As noted by D.C.I. Thienpont et al. Nature, 209, 1084–6, (1966), British Pat. No. 1,043,489, A.H.M. Raeymaekers et al., J. Med. Chem., 9, (4), 545–555 (1966), and British Pat. No. 1,076,109, Tetramisole has valuable pharmacological properties, and is used as a potent broad-spectrum antihelminthic. Recently, the interest in this agent has considerably increased because of the discovery of its immunoregulating properties, and the use of the drug in the therapy of neoplastic diseases (the Ger. Offen, No. 2,340,632).

Antidepressive (the Ger. Offen. No 2,340,634) and antianergic (the Ger. Offen. No. 2,340,633) activities of R,S-2,3,5,6-tetrahydro-6-phenylimidazo(2,1-b) thiazole and its pharmacologically active salts have also been described.

The Ger. Offen. No. 2,236,970 describes the compound R,S-[2-(2-hydroxyethylamino)-1-phenyl]-ethylanine+, having Formula II

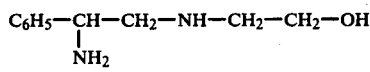

wherein a five step synthesis, including the use of reagents such as hydrogen chloride, thionyl chloride, ammonium thiocyanate, and two thermal cyclizations, results in obtaining of Tetramisole, of Formula I. *L6
+Another possible name of the compound with Formula II is R,S-α-(2-hydroxyethylaminomethyl)-benzylamine.

The object of the present invention is to provide R,S-[2-(2-hydroxyethylamino)-1-phenyl]-ethylamine derivatives which enable a new and highly effective method of synthesis of R,S-2,3,5,6-tetrahydro-6-phenyl-imidazo(2,1-b)-thiazole, of Formula I.

According to this invention, the new R,S-[2-(2-hydroxyethylamino)-1-phenyl9 -ethylamine derivatives are of Formula III

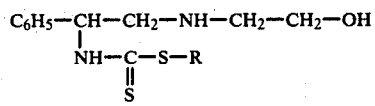

wherein R represents hydrogen, hydrocarbon radicals containing a double or triple bond, or arylaliphatic type groups.

Those derivatives, of Formula III, wherein R represents hydrogen, allyl (prop-2-en-1-yl), propargyl (prop-2-in-1-yl), or benzyl are preferred.

R,S-[2-(2-hydroxyethylamino)-1-phenyl]-ethylamine derivatives are synthesized by interacting R,S-[2-(2-hydroxyethylamino)-1-phenyl]-ethylamine (II) with carbon disulfide, and the compound obtained, of Formula III, wherein R is hydrogen is then reacted with alkyl halides having allyl, propargyl or benzyl groups in aqueous, aqueous-organic, or organic medium, producing ester-amides of the dithiocarbonic acid.

The R,S-N-[2-(2-hydroxyethylamino)-1-phenyl]-ethylamide of the dithiocarbonic acid, of Formula III, wherein R represents hydrogen, can also exist in the form of an internal dithiocarbamic salt of Formula IV

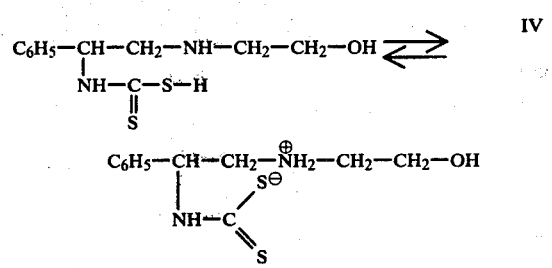

These R,S-[2-(2-hydroxyethylamino)-1-phenyl]-ethylamine, derivatives, allow for a method, easily accomplished, for example: by heating, giving good yields of R,S-1-(2-hydroxyethyl)-4-phenyl-imidazolidine-2-thione (V), which is dehydrated quantitatively, giving R,S-2,3,5,6-tetrahydro-6-phenyl-imidazo(2,1-b)-thiazole (Tetramisole) (I), as described in the Bulgarian author's certificates; Nos. 24864 and 25138.

According to this invention, the derivatives of R,S-[2-(2-hydroxyethylamino)-1-phenyl]-ethylamine, and especially R,S-N[2-(2-hydroxyethylamino)-1-phenyl]-ethylamide of the dithiocarbonic acid (IV), have the advantage of easily forming the Tetramisole heterocyclic ring system, employing a three-step synthesis.

This invention is explained by the following examples:

EXAMPLE 1

1. R,S-N[2-(2-hydroxyethylamino)-1-phenyl]-ethylamide of the dithiocarbonic acid (IV).

18 g (0.10 moles) of R,S-[2-(2-hydroxyethylamino)-1-phenyl]-ethylamine were dissolved in 60 ml of 96% ethanol. After a homogeneous solution was obtained, 11,4 g (0.15 moles) of carbon disulfide were added dropwise at 40° C. After a period of four hour heating under reflux, the precipitate which separated was filtered and washed with 10 ml of ethanol. The R,S-N-[2-(2-hydroxyethylamino)-1-phenyl]-ethylamide of the dithiocarbonic acid yield was 18.1 g (70% of the theoretical); m.p. 136°–138° C. (decomp.).

Elemental analysis of $C_{11}H_{16}N_2OS_2 (M=256.38)$

| Element | Calculated % | Found % |
| --- | --- | --- |
| C | 51.52 | 51.95 |
| H | 6.29 | 6.35 |
| N | 10.93 | 10.70 |
| S | 25.01 | 24.80 |

EXAMPLE 2.

R,S-N-[2-(2-hydroxyethylamino)-1-phenyl]-ethylamide-S-allyl ester of the dithiocarbonic acid. 25.6 g (0.10 moles) of R,S-N-[2-(2-hydroxyethylamino)-1-phenyl]-ethylamide of the dithiocarbonic acid (Example 1) were suspended in 100 ml of water. The suspension was added to 100 ml 5% aqueous solution of sodium hydroxide, and the resulting mixture was filtered through an asbestos-cellulose filter. 14.5 g (0.12 moles) of allyl bromide were added to the filtrate, and the mixture stirred for one hour at room temperature. 100 ml of methylene chloride were added to the mixture, separating and filtrating the crystals obtained. 8.7 g of R,S-N-[2-(2-hydroxyethylamino)-1-phenyl]-ethylamide-S-allyl ester of the dithiocarbonic acid were obtained; m.p. 124°–126° C. Yield—32% of the theoretical.

Infrared spectrum: Nujol ®mull (CH=CH$_2$)=1625 cm$^{-1}$.

Elemental analysis of $C_{13}H_{18}N_2OS_2$ (M=282.42).

| Element | Calculated % | Found % |
|---|---|---|
| C | 55.31 | 55.01 |
| H | 6.38 | 6.70 |
| N | 9.92 | 10.20 |
| S | 22.69 | 22.93 |

EXAMPLE 3.

R,S-1-(2-hydroxyethyl)-4-phenyl-imidazolidine-2-thione (V). (Cyclization by melting of a compound, with Formula IV).

97 g (0.38 moles) of R,S-N-[2-(2-hydroxyethylamino)-1-phenyl]-ethylamide of the dithiocarbonic acid (Example 1) were heated at 150° C. for four hours. 120 ml of methylene chloride were added to the melt, and cooled to 20° C. The solution was filtered, the filtrate extracted with 120 ml of 10% aqueous potassium hydroxide solution, and washed with 120 ml hydrochloric acid (1:3). The methylene chloride extract was washed with water to adjust pH=5, and dried over an anhydrous sodium sulfate. After distilling the solvent off, 42 g of R,S-1-(2-hydroxyethyl)-4-phenyl-imidazolidin-2-thione were obtained; m.p. 91°–93° C. yield—50% of the theoretical.

EXAMPLE 4.

R,S-1-(2-hydroxyethyl)-4-phenyl-imidazolidine-2-thione (V). (Cyclization by melting R,S-N[2-(2-(2-hydroxyethylamino-1-phenyl]-ethylamide-S-allyl ester of the dithiocarbonic acid). 8.7 g (0.032 moles) of R,S-N-[2-(2-hydroxyethylamino-1-phenyl]-ethylamide-S-allyl ester of the dithiocarbonic acid were heated for two hours at 150° C. After cooling the mixture to room temperature, 50 ml of methylene chloride were added and the solution obtained, filtered through an asbestos-cellulose surface. The filtrate was initially washed with 25 ml 10% aqueous solution of sodium hydroxide, then with 25 ml aqueous solution of hydrochloric acid (1:3), and in the end, with 50 ml of water to adjust pH=6. The extract of methylene chloride was dried over anhydrous sodium sulfate. 2.47 g of crude R,S-1-(2-hydroxyethyl)-4-phenyl-imidazolidine-2-thione were obtained after distilling the methylene chloride. R,S-1-(2-hydroxyethyl)-4-phenyl-imidazolidine-2-thione, recrystallized from methylene chloride, had m.p. 91°–93° C. Yield—34% of the theoretical.

EXAMPLE 5.

R,S-2,3,5,6-tetrahydro-6-phenyl-imidazo(2,1-b)-thiazole hydrochloride. (Cyclodehydration with hydrochloric acid).

11.2 g (0.05 moles) of R,S-1-(2-hydroxyethyl)-4-phenyl-imidazolidine-2-thione were dissolved on stirring in 100 ml of hydrochloric acid, the reaction mixture obtained was heated under reflux for three hours, and the solvent distilled under reduced pressure off. The crude material was suspended in 40 ml of isopropanol and filtered. The yield of R,S-2,3,5,6-tetrahydro-6-phenyl-imidazo(2,1-b)-thiazole hydrochloride was 11.6 g; m.p. 256°–258° C. Yield—quantitative.

What we claim is:

1. An R,S-[2-(2-hydroxyethylamino)-1-phenyl]-ethylamine of the formula III

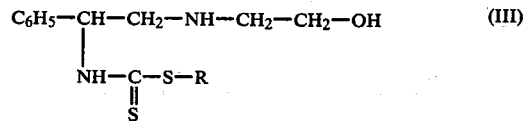

wherein R represents hydrogen or allyl,

2. R,S-N-[2-(2-hydroxyethylamino)-1-phenyl]-ethylamide of the dithiocarbonic acid.

3. R,S-N-[2-(2-hydroxyethylamino)-1-phenyl]-ethylamide-S-allyl ester of the dithiocarbonic acid.

4. A process of obtaining a compound of formula III

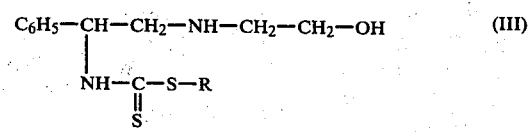

comprising the steps of reacting R,S-[2-(2-hydroxyethylamino)-1-phenyl]-ethylamine with carbon disulfide to form the R,S-N-[2-(2-hydroxyethylamino)-1-phenyl]-ethylamide of dithiocarbonic acid which is then reacted with an allyl bromide to yield the compound of formula III.

* * * * *